US010076234B2

(12) United States Patent
Duan et al.

(10) Patent No.: US 10,076,234 B2
(45) Date of Patent: Sep. 18, 2018

(54) APPARATUS AND METHOD FOR CONTROLLING MOVEMENT OF A CAPSULE ENDOSCOPE IN DIGESTIVE TRACT OF A HUMAN BODY

(71) Applicant: ANKON TECHNOLOGIES CO., LTD, Wuhan (CN)

(72) Inventors: Xiaodong Duan, Plansaton, CA (US); Guohua Xiao, Plano, TX (US); Xinhong Wang, San Diego, CA (US)

(73) Assignee: ANKON TECHNOLOGIES CO., LTD., Wuhan ( * ) Notice: Subject to any disclaimer, the term of this patent is extended or adjusted under 35 U.S.C. 154(b) by 763 days.

(21) Appl. No.: 14/486,131

(22) Filed: Sep. 15, 2014

(65) Prior Publication Data

US 2015/0018615 A1    Jan. 15, 2015

Related U.S. Application Data

(63) Continuation-in-part of application No. PCT/CN2013/076162, filed on May 23, 2013.

(30) Foreign Application Priority Data

Apr. 18, 2013 (CN) .......................... 2013 1 0136094

(51) Int. Cl.
*A61B 1/00* (2006.01)
*A61B 1/04* (2006.01)
(Continued)

(52) U.S. Cl.
CPC ...... *A61B 1/00158* (2013.01); *A61B 1/00006* (2013.01); *A61B 1/00149* (2013.01);
(Continued)

(58) Field of Classification Search
CPC .......... A61M 25/0127; A61M 25/0158; A61B 1/00158; A61B 1/041; A61B 34/20;
(Continued)

(56) References Cited

U.S. PATENT DOCUMENTS

2007/0221233 A1    9/2007  Kawano
2013/0303847 A1*  11/2013  Sitti ................... A61B 1/00158
                                                        600/104

FOREIGN PATENT DOCUMENTS

CN    200680049622.6    1/2009
CN    200910106020.6    9/2010
(Continued)

*Primary Examiner* — Timothy J Neal
*Assistant Examiner* — Aaron B Fairchild
(74) *Attorney, Agent, or Firm* — Treasure IP Group., LLC

(57) ABSTRACT

System and method to provide a suspended capsule endoscope at a liquid gas interface is described. The capsule comprises a permanent magnetic dipole and has a density greater than the density of the liquid. An sphere-shaped external magnet is used to suspend and control the movement of the capsule endoscope at the liquid/gas interface. The capsule endoscope can translate along variable axes, rotate and tilt, according to the movement of the external magnet. The external magnet performs a translation and rotation simultaneously to keep the capsule endoscope still and anchored at the same position of the liquid/gas interface. The external magnet adjusts its distance to the liquid/gas interface during the rotation in order to apply a constant magnetic field force to the capsule endoscope.

5 Claims, 10 Drawing Sheets

(51) Int. Cl.
*A61B 34/00* (2016.01)
*A61M 25/01* (2006.01)

(52) U.S. Cl.
CPC .............. *A61B 1/041* (2013.01); *A61B 34/73* (2016.02); *A61M 25/0127* (2013.01)

(58) Field of Classification Search
CPC .............. A61B 34/73; A61B 2034/731; A61B 2034/732; A61B 2034/733
See application file for complete search history.

(56) References Cited

FOREIGN PATENT DOCUMENTS

| | | |
|---|---|---|
| CN | 200980113659.5 | 4/2011 |
| CN | 201210156821.X | 9/2012 |
| CN | 103222842 | 7/2013 |
| DE | 102011006325 | 10/2012 |
| EP | 2353489 | 8/2011 |
| WO | 2013168710 | 11/2013 |

\* cited by examiner

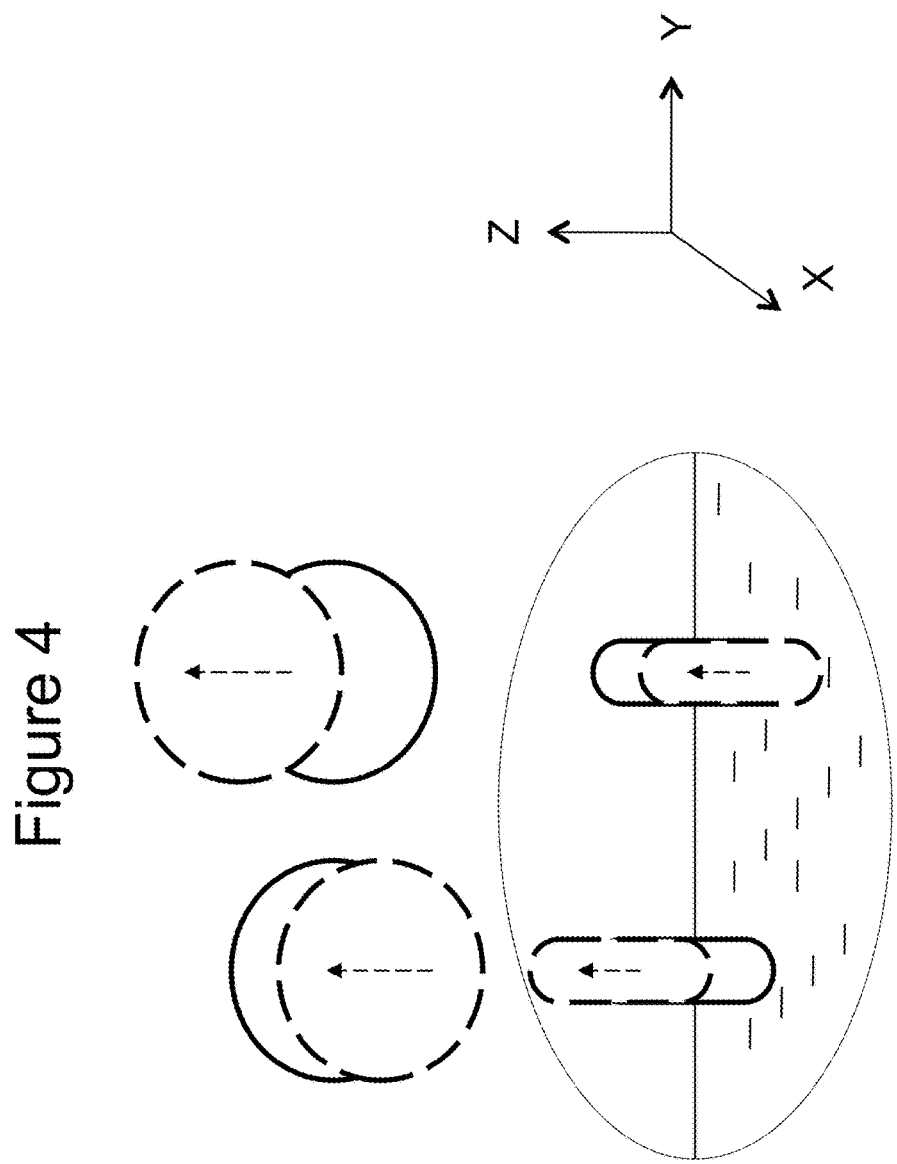

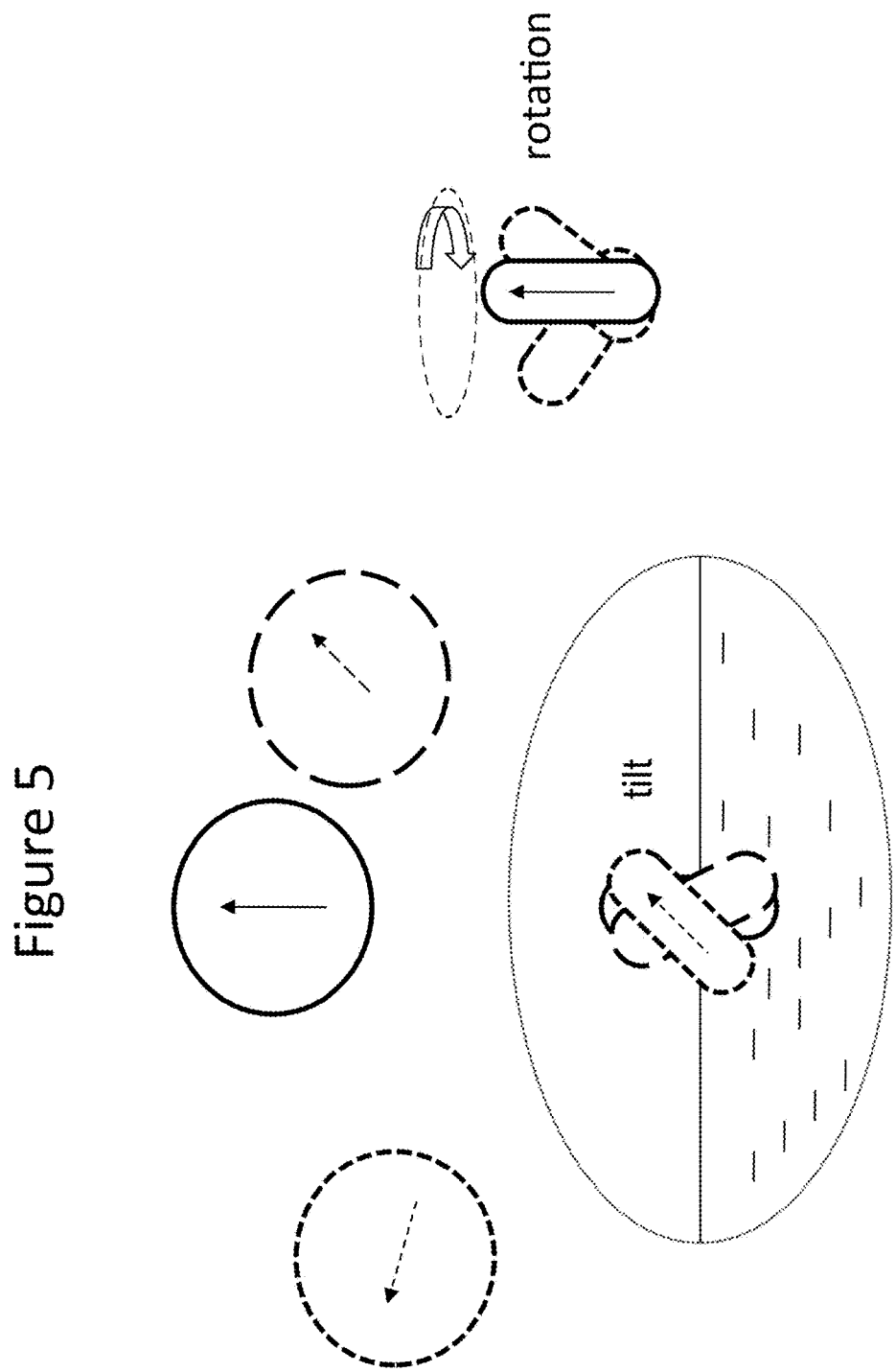

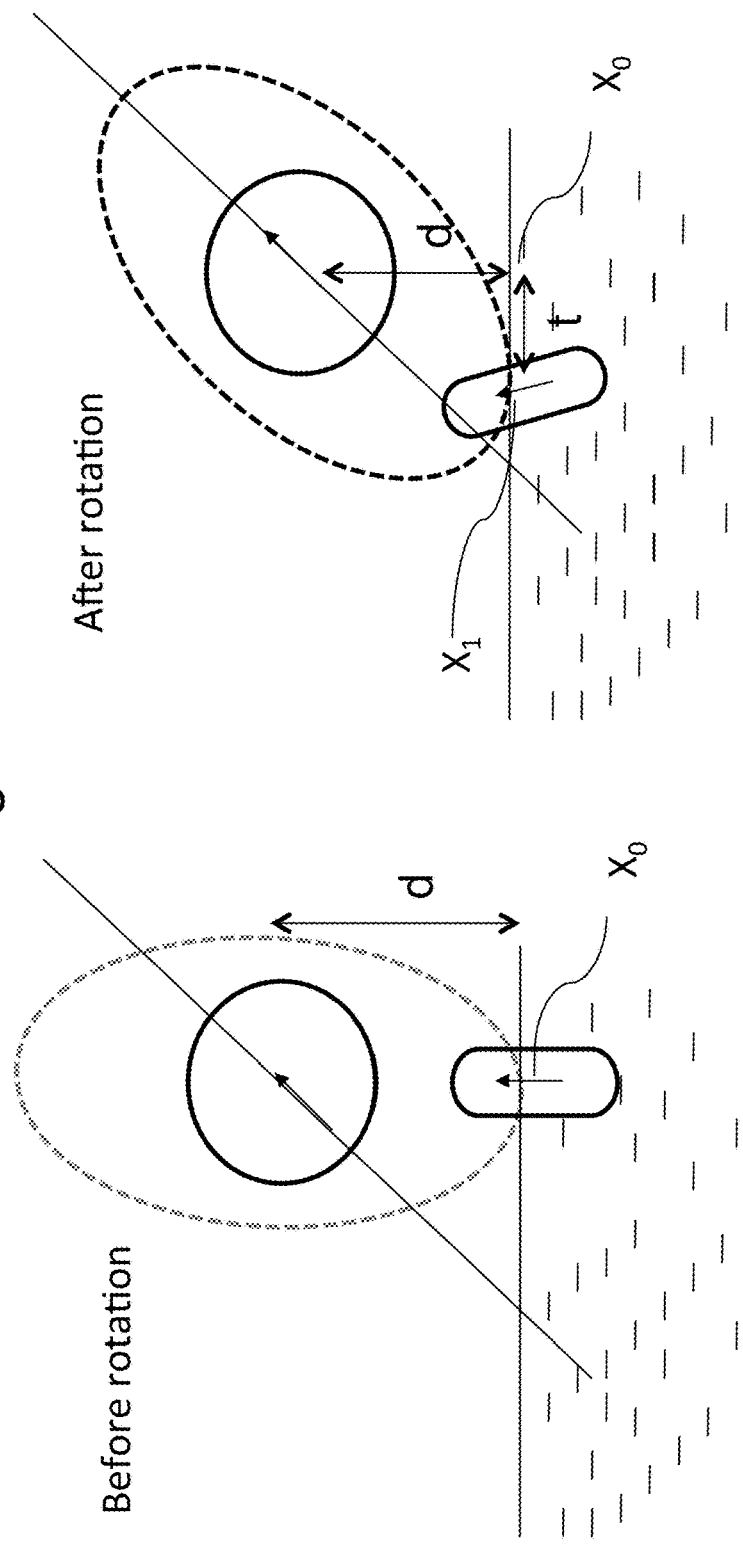

APPARATUS AND METHOD FOR CONTROLLING MOVEMENT OF A CAPSULE ENDOSCOPE IN DIGESTIVE TRACT OF A HUMAN BODY

CROSS REFERENCE TO RELATED APPLICATIONS

This application is a continuation of PCT application PCT/CN2013/076162 filed on May 23, 2013. The PCT application is incorporated herein by reference.

TECHNICAL FIELD

The invention relates to medical apparatus and instruments, specifically refers to a system and method to control movement of a capsule endoscope in a human GI track.

BACKGROUND OF THE INVENTION

With the development of large-scale integrated circuit technology, MEMS, wireless communications and optical technology, capsule endoscope has been used as an effective way for diagnosis for intestinal diseases. M2A produced by Given Imaging, a company in Israel, Endo Capsule researched and developed by Olympus Company in Japan, and products marketed under a Chinese company, Jinshan Science and Technology, all have taken significant market shares in the capsule endoscope marketplace. The current available wireless capsules adopted in the medical field are carried by peristalsis through a human digestive tract, as a result the movement speed, movement direction and capsule location is random, which makes it difficult for medical doctors to collect the relevant information for intestinal tract diagnosis.

If positioning and controlling a capsule endoscope in vivo cannot be achieved, navigating it through a human GI track for traversal intestinal diagnosis/examination face multiple issues. Current existing capsule endoscopes mainly rely on peristalsis and organs contraction to accomplish the capsule movement along a GI track in vivo. Such movement is not only slow, leading to low detection efficiency and potential dead zones in the examination, but also makes examination or operation in specific disease region impossible, as the movement based on peristalsis cannot move the capsule endoscope back and forth to a precise target location for a stable examination or operation, and such movement does not allow control of movement speed and direction, and the posture.

Chinese domestic Jinshan Group has manually controlled an external magnet to accomplish the position or navigation of a capsule endoscope in GI track. The manual control is low cost, but is less precise than a mechanical robot thus less favorable in a routine testing, which prefers artificial intelligence. Furthermore, several scientific research institutions have demonstrated controlling a magnetic capsule endoscope by a strip shaped external magnet. This method is quick and can precisely place the capsule in a direct route, however, because human GI track is not straight but very snaky, it is very difficult to carry out actual positioning of capsule endoscope using such linear magnet in practical clinical setting.

US patent applications Ser. Nos. US20070221233, 20100268026, 20110054255, and 20110184235 disclosed a floating or suspended capsule. As described in these patent applications, a magnetic capsule is suspended by a surrounding liquid, which requires the density of the capsule to be less than the liquid. In clinical practice, since the most commonly used liquid is water, the weight of such floated capsule is limited to be under 3 g. If a capsule is equipped with a permanent magnetic dipole to achieve better positioning, the weight of the capsule unfortunately easily go over 3 g. For a capsule endoscope whose density is more than water and perhaps weight is over 3 g, how to realize stable suspension has not been disclosed.

SUMMARY OF THE INVENTION

The present invention overcomes the technology difficulties in the prior arts, and provides a system and method to control the movement of a capsule endoscope in a human GI track. The system and method disclosed herein, is capable to precisely generate a 5-dimensional moving and rotational magnetic field, to remotely apply force to a magnetic capsule endoscope, which is suspended in a liquid gas interface.

In a first aspect of the present invention, a capsule endoscope includes a capsule-shaped housing and an imaging unit that is arranged inside the capsule-shaped housing in a fixed manner, and takes an image of an inside of an organ by the imaging unit in a state where the capsule endoscope is suspended at a liquid/gas interface. The liquid and gas is introduced inside the organ of a subject. In one embodiment of the present invention, the capsule endoscope suspended at the liquid/gas interface comprises a permanent magnetic dipole, wherein the capsule endoscope has a mass center and the permanent magnetic dipole inside the capsule endoscope has a magnetic center. The capsule endoscope changes its position or orientation by interacting with an external magnetic.

In one embodiment of the present invention, the density of capsule endoscope is greater than the density of the liquid. In another embodiment of the present invention, the mass of the capsule endoscope is greater than 3 g.

In another embodiment of the present invention, the distance between the magnetic center and mass center of capsule endoscope is less than 2 mm.

In a second aspect of the present invention, a method to use a capsule endoscope having a permanent magnetic dipole is disclosed. The method comprises a step to rotate the capsule endoscope locally when the capsule endoscope forms a tilt angle at a liquid/gas interface to observe an internal organ. The method comprises providing a capsule endoscope comprising a permanent magnetic dipole and a camera;
suspending the capsule endoscope at the liquid/gas interface;
applying magnetic field to the permanent magnet dipole through an external magnet;
changing the tilt angle of the capsule endoscope while being suspended at the same position at the liquid/gas interface by rotating and moving the external magnet along one or more axially directions; and
receiving constant magnetic field force by the permanent magnetic dipole.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 4 is a schematic illustration of a cross section view of the system disclosed herein, wherein the capsule endoscope moves vertically in response to a vertical movement of the external magnetic;

FIG. 5 is a schematic diagram of a cross section view of the system disclosed herein, to explain a desired rotational operation of the capsule endoscope inside an organ while being suspended at an gas/liquid interface, wherein combinational movements of the external magnet only change the tilt angles of the capsule leaving its position at the liquid/gas interface mostly unchanged;

FIG. 6 is a schematic diagram of a cross section view of the system disclosed herein, explaining a simple rotation of the external magnet causes the capsule endoscope to move away from its original position, more than a simple rotation at its original position, when the capsule is being suspended at the gas/liquid interface;

DETAILED DESCRIPTION OF THE PREFERRED EMBODIMENTS

Figure 1:
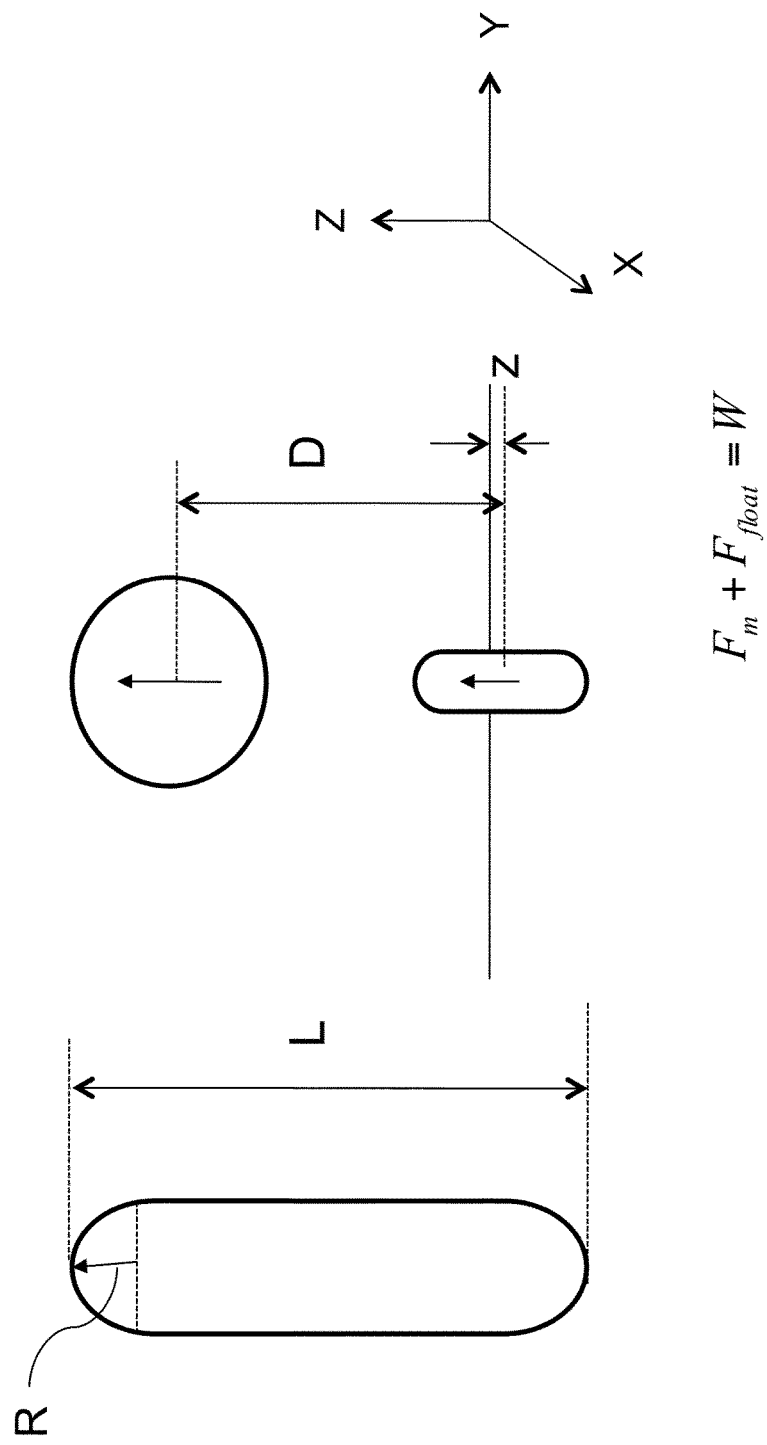
FIG. 1 is a schematic diagram showing an example of a capsule endoscope according to one aspect of the present invention.

Exemplary embodiments of a capsule endoscope according to the present invention are explained in detail below with reference to the accompanying drawings. The present invention is not limited to the embodiments.

Ingestible wireless medical capsules are known in the medical arts. Such wireless capsule is swallowed and travels through the digestive tract, collecting and transmitting data during the course of its journey, can also collecting images if equipped with cameras. When a capsule endoscope is equipped with a permanent magnetic dipole, the capsule endoscope can be parked at a target location for a desired period of examination.

It is one object of the present invention to place a capsule endoscope in a precise location in a target area, which maybe a disease area, and collect real-time medical related information so that the medical doctors can easily perform diagnose or operation on that precise target location.

Further when the capsule endoscope is positioned at the target location, the capsule endoscope needs to be fixed at the target location, substantially stable, for a specific period of time, in order to be collect accurate information or non blurred images. Stable, herein, refers to a status of the capsule, which can maintain its position and orientation without a change, or a detectable change, or a noticeable change can be ignored in a desired applicable experimental or clinical settings. The capsule endoscope, in accordance with the present invention, comprises a permanent magnetic dipole. The magnetic dipole is a vector. The location of a capsule endoscope as referred to in the present invention, includes its location with respect to a reference, and angles with respect to some reference. The orientation of a capsule endoscope includes its direction with respect to some reference. The target location, herein, include a liquid and gas, having a definable liquid/gas interface.

In one embodiment, the capsule endoscope can be stable for at least the time duration for taking an image with an acceptable resolution or performing a simple test or procedure.

Since various prior arts have provided multiple ways to navigate a capsule endoscope into a precise location, the system and methods, disclosed in the present invention, are mostly directed to how to use the external magnet to change the orientation of the capsule while it is being suspended in a stable state at a desired location.

System disclosed herein comprises a capsule endoscope, which is placed in a target area, consisting essentially of a liquid and a gas. The capsule endoscope includes a capsule-shaped housing and an imaging unit that is arranged inside the capsule-shaped casing in a fixed manner, and takes an image of an inside of target area, by the imaging unit in a state where the capsule endoscope is suspended in a liquid/gas interface. In one embodiment of the present invention, the capsule endoscope suspended at the liquid/gas interface comprises a permanent magnetic dipole, wherein the capsule endoscope has a mass center and the permanent magnetic dipole has a magnetic center. The capsule endoscope changes its position or orientation by interacting with an external magnetic.

In one example, the target area is an internal organ. In one instance, the target area is a stomach. In another example, stomach is partially filed with a liquid.

In one example, the liquid and gas are introduced to the target area after the target area has been vacated. In one example, the liquid is water. In another example, gas is air. In still another example, gas is air with additional $CO_2$, which is generated by oral acrogenic powder.

The present invention is directed to a capsule endoscope being suspended at a liquid/gas interface. "Being suspended at a liquid/gas interface" does not suggest a limitation on the partition of the capsule in either the liquid or the gas phase. Within the scope of the present invention, as long as the capsule experienced a floating force from the liquid, then the capsule is considered to be as suspended, which includes the capsule is completely immersed and the capsule is mostly exposed, thought these examples are not the best modes to use the present invention.

The capsule endoscope in the present invention has a housing. The capsule endoscope can be of any shape or in any size of a pill as in the general art. In one example, the capsule is cylindrical shaped with hemispherical ends, spherical, capsule shaped but with size of one end larger than the other end, or an American football shaped. The capsule endoscope in the present invention is preferred to be symmetrical along its length direction. The capsule endoscope has a mass center, which is the weight center when measured in the air, inherit with the structure of the capsule endoscope and cannot be changed because of the environment it is placed in. The capsule endoscope comprises a permanent magnetic dipole, which also has a center of magnetic moment, which is referred as a center of the magnetic dipole.

The capsule endoscope disclosed herein, has a density, which is an inherent property of the capsule due to the material and structural components and does not change because of the environment it is placed in. Unlike most of floating capsule endoscopes disclosed in the prior arts, which requires a density to be less than the density of the liquid, normally 1, the density of the capsule endoscope of the present invention is required to be more than the liquid density, in order to be successfully and accurately suspended at a target location.

System disclosed herein comprises an external magnet, generating an external magnetic field, 5-dimensional moving and rotational magnetic field, to remotely apply force to a magnetic capsule endoscope.

Referring to FIG. 1, a capsule endoscope in a stable suspension state is schematically illustrated. In this example, as shown, the capsule endoscope is a basic three-dimensional geometric shape consisting of a cylinder with hemispherical ends. Said capsule has a length of L and a radius of R for the semi-sphere end. The capsule endoscope has a permanent magnetic dipole, positioned inside the cylinder portion of the capsule endoscope. Said magnetic dipole of capsule endoscope has a magnetic moment of m. The capsule endoscope may further comprise one or more image devices. The image device, in one example is a camera. The camera may be positioned at the end of the capsule endoscope. When there are two cameras positioned on the capsule endoscope, preferably, the two cameras are position at opposite ends of the camera. The system further comprises an external magnetic, which is sphere shaped, having a magnetic moment M.

Such a capsule endoscope, suspended at the liquid/gas interface, is subjected to three forces, the gravity of capsule (W), the magnetic force ($F_m$) from the external magnetic field, and a floating force ($F_{float}$) from the liquid. In the stable suspension state, the capsule is supported by the floating force ($F_{float}$), and external magnetic field force ($F_m$). The weight of the capsule (W), floating force ($F_{float}$) and magnetic force ($F_m$) has the following relationship (Eq.1).

$$F_m + F_{float} = W \quad \text{Eq. 1}$$

$$F_m = \frac{\mu_o}{4\pi} \frac{6Mm}{(D+z)^4} \quad \text{Eq. 2}$$

$$F_{float} = \rho_{liquid}(L/2 + z)\pi R^2 \quad \text{Eq. 3}$$

Further, under the same condition, floating force ($F_{float}$) and external magnetic filed force ($F_m$) are established as in equations 2 and 3. Wherein M is the magnet moment of the external magnet in the system, m is the magnetic moment of the magnetic dipole in the magnetic capsule. D is the vertical distance from the magnetic center of the external magnet dipole to the magnetic center of the magnetic capsule; z is the vertical distance between the liquid-air interface and the magnetic center of the capsule as in FIG. 1.

When stable suspension is established, the following conditions (Eq. 4 and Eq.5) are met.

$$\frac{\partial(W - F_m - F_{float})}{\partial z} = \frac{\mu_0}{\pi} \frac{6Mm}{(D-L/2)^5} - \rho_{liquid}\pi R^2 < 0 \quad \text{Eq. 4}$$

$$D/L > 4\rho_{capsule}/\rho_{liquid} + 1/2 \quad \text{Eq. 5}$$

Figure 2:
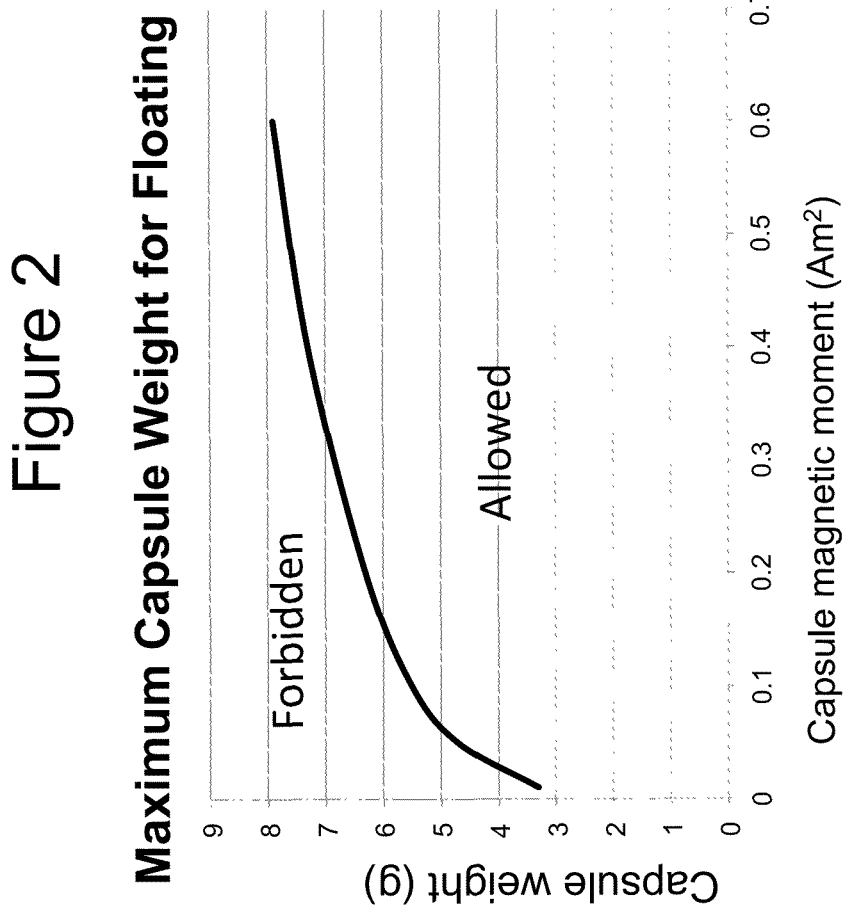
FIG. 2 is a relationship between a capsule weight and capsule magnetic moment, explaining the maximum allowable weight for the capsule endoscope in order to achieve stable suspension, in accordance with one aspect of the present invention.

Therefore, the maximum capsule weight allowed (W) in order to achieve a stable suspension can be derived based on Equations 1-5. FIG. 2 sets up critical configuration limitation of the capsule endoscope in accordance with the aspects of the present invention. The magnetic moment (m) of the magnetic dipole in the capsule endoscope and the weight of the capsule endoscope have to meet the relationship requirement of FIG. 2 in order to be able to a functional and useful suspended capsule endoscope system. In FIG. 2, the area underneath the curve is an allowed region and the area above the curve is a forbidden region. FIG. 2 suggests that, in a system having an external magnet with a magnetic moment at 2000 (Am^2), when the magnetic moments of the magnetic dipole inside capsule endoscope is between 0.01-0.6 (Am^2), the weight of capsule need to be between 3-8 g in order to be suspended. In one perspective to design a capsule endoscope having a known and fixed magnetic moment, FIG. 2 depicts a weight limitation. In another words, in one example, when the capsule magnetic moment is at 0.1 (Am^2), the weight of capsule needs to be fewer than 6 g, otherwise the capsule will be too heavy for suspension. In another example, when the capsule magnetic moment is at 0.2 (Am^2), the weight of capsule needs to be fewer than 6.2 g; otherwise the capsule will be too heavy for suspension. In another example, when the capsule magnetic moment is at 0.3 (Am^2), the weight of capsule needs to be fewer than 7 g; otherwise the capsule will be too heavy for suspension. In another example, when the capsule magnetic moment is at 0.4 (Am^2), the weight of capsule needs to be fewer than 7.5 g, otherwise the capsule will be heavy for suspension. In another example, when the capsule magnetic moment is at 0.5 (Am^2), the weight of capsule needs to be fewer than 7.8 g; otherwise the capsule will be too heavy for suspension. In another example, when the capsule magnetic moment is at 0.6 (Am^2), the weight of capsule needs to be fewer than 8 g; otherwise the capsule will be too heavy for suspension.

On the other hand, in some uncommon examples, when configuring a capsule endoscope to have a desired weight or a weight range, FIG. 2 suggests a limitation of the corresponding strength of the magnetic dipole in the capsule endoscope. In one example, when the weight target of a capsule is about 5 g, the magnetic moment of the capsule endoscope needs to be greater than 0.05 (Am^2). In another example, when the weight target for a capsule is about 6 g, the magnetic moment of the capsule endoscope needs to be greater than 0.15 (Am^2). In another example, when the weight target for a capsule is about 7 g, the magnetic moment of the capsule endoscope needs to be greater than 0.3 (Am^2). In another example, when the weight target of a capsule is 8 g, the magnetic moment of the capsule endoscope needs to be greater than 0.55 (A/cm^2).

In the aforementioned examples, it is disclosed a stationary system, wherein the external magnet is stationed with robotic arms with a magnetic moment. Equations 1-5 and FIGS. 1 and 2, suggests how to change the capsule weights or magnetic moments under different circumstances, in order to achieve a stable system. But the aforementioned example should be construed as a limitation. Instead, Equations 1-5 can also be used to design a system that having a capsule endoscope having a fixed weight and magnetic moment, the external magnet can be changed under different circumstance. Like for example, in a portable system, wherein the external magnet is a hand held device, although it may not be a preferred application of the present invention.

Figure 3:
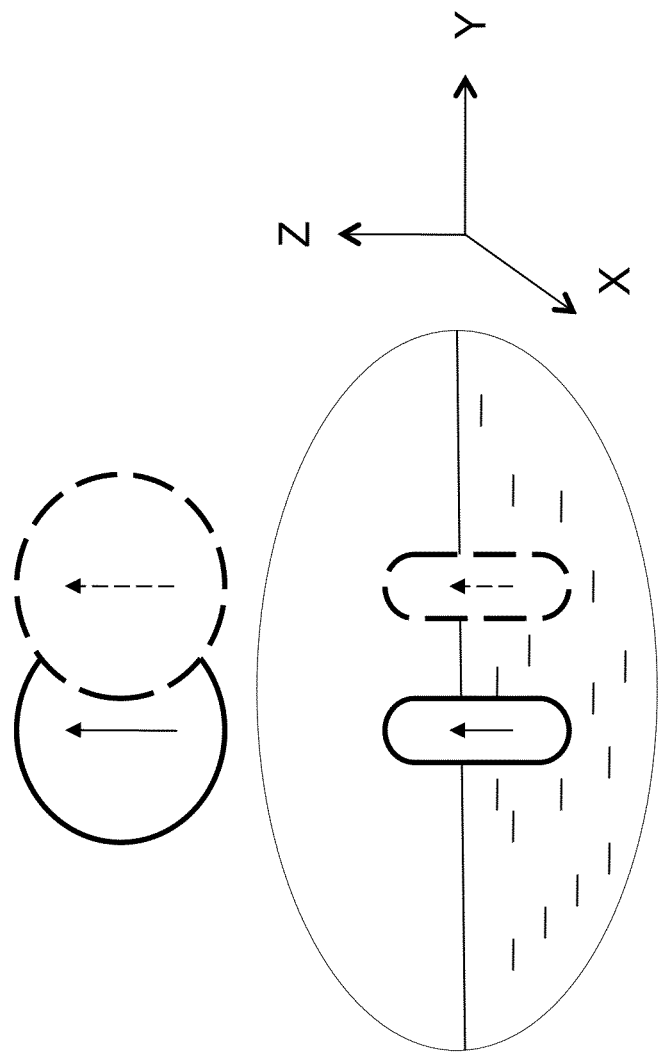
FIG. 3 is a schematic illustration of a cross section view the system disclosed herein, wherein the capsule endoscope moves horizontally in response to a horizontal movement of an external magnetic.

Referring to FIGS. 3 and 4, the present invention is directed to a magnetic endoscope system having an external robotic magnet, wherein the capsule endoscope can be suspended in a liquid in a vivo area, the density of the capsule endoscope is greater than the density of the liquid therein. Without the applied force ($F_m$) from the external robotic magnet, the capsule will not be able to suspend or float in the liquid. In another words, the capsule endoscope only moves in response to the movement of the external magnet. As shown in FIG. 1, the magnet capsule endoscope follows the external magnetic to navigate in a XY plane. When the external magnet performs a translation, the magnetic capsule does the same in response to the magnetic field force. In the XY plane, the magnetic endoscope travels in the same direction of the movement of the external robotic magnet. When the external robotic magnet moves to the right, the capsule endoscope also moves to the right. When the external robotic magnet moves to the front, the capsule endoscope also moves to the front, which is illustrated as X direction. When the external magnet performs a translation, the magnetic capsule does the same to follow the magnetic field force.

The magnet capsule endoscope can also moves vertically, along a namely z direction as illustrated in FIG. 4. In one embodiment of the present invention, a patient lies flat on a surface along the XY plane and a capsule endoscope is placed inside the stomach of the patient. The capsule endoscope is suspended in the liquid or at liquid/air interface. When the external robotic magnet moves up and down vertically, capsule endoscope moves vertically too in response to the change of location of the external robotic magnet. Contrary to the movement path illustrated FIG. 3 wherein the capsule endoscope moves in the same direction of the external robotic magnet, FIG. 4 illustrates the magnetic capsule endoscope moves in the opposite direction of movement of the external robotic magnet. When the external robotic magnet moves down, it bring the external magnetic field closer to the magnetic dipole in the capsule endoscope, the capsule endoscope is attracted to move up. When the external robotic magnet moves up, it moves away from the magnetic capsule endoscope, the magnetic field weaken as the external magnetic moves up, and the capsule endoscope moves down. By controlling the movement of the external robotic magnet along the vertical or z direction, the capsule's position along z direction can be precisely controlled. When examining a stomach, the capsule can be conveniently positioned to first have a remote view followed by a closer view of the gastric mucosa for the top or bottom wall of thereof.

Besides translation along three axes as shown in FIGS. 3-4, the magnetic capsule endoscope can also perform rotational movements, including tilts and revolutions under the influence of the external magnetic field generated by the external robotic magnet. In a clinical environment, tilts and revolutions are necessary for the doctor to examine a broader view of the stomach while being suspended as anchored in an elevated position. FIG. 5 shows the difference between a tilt and revolution movement.

When the capsule endoscope in the present invention is suspended at a liquid/gas interface, the capsule forms an angle with the liquid/gas interface. Said angles are referred as a tilt angle. The tilt angle is between 0-360 degrees in accordance with the present invention. In one example, said tilt angle is between 45-135 degrees to allow easy and accurate orientation.

In accordance with the aspects with the present invention, rotation or rotation movements mean the magnetic capsule endoscope changes its orientation in either a 2D plane or a 3D space. Rotation or rotational movements include both a tilt, changing the angle between the capsule and gas/liquid interface in a 2D plane, and a revolution, changing the angle between the capsule and gas/liquid interface in a 3D space, wherein the position of the capsule endoscope at the liquid/gas interface is not changed during the movement process, but the tilt angle or the tilt angle in a 2D cross sectional view of the revolution is changed before and after the rotation. In one embodiment, rotational movement is a tilt. Tilt occurs in a plane of z axis and the vertical rotational magnetic moment of the sphere shaped magnet, as shown in FIG. 5, wherein the capsule changes its tilt angle like a hand in a clock. In another embodiment, rotation movement is a revolution. Revolution occurs in a xyz space, wherein the capsule endoscope revolves around its anchor position at the liquid/gas interface as shown in FIG. 5. While the capsule endoscope revolves according to the horizontal projection in xy-plane of the magnetic moment of the sphere shaped external magnet. In FIG. 5, the angle between the long axis of the capsule endoscope and the surface of the liquid and air interface is kept the same during the revolution. In a cross sectional view of a revolution, the projection of the angle formed between the long axis of the capsule and liquid/gas interface changes in accordance with the movement of the external magnet.

For clarify purpose, tilt means the capsule endoscope does not changes its position in the xyz coordinates, but just change the angle between the capsule's long axis and the gravity direction, which is perpendicular to the air/liquid interface. In accordance with the aspects with the present invention, revolution means the capsule endoscope also does not change its position in the xyz coordinates, but changes the direction of the capsule's long axis along liquid/gas interface, which results in a change of tilt angle in its corresponding 2D cross sectional view.

Unlike the translation movement, wherein a one-step operation of the external robotic magnet can help to navigate the capsule endoscope into a target location; rotational movement is a more complicated process. When the external robotic magnet rotates, an established stable suspension system will be perturbed in many aspects. The maximum magnetic field position at the liquid/gas interface, the external magnetic filed strength at the liquid/gas interface, and the external magnetic field direction (or angle) will all change. The external magnet would have to 1) translate while rotate to keep the capsule endoscope still (FIGS. 6 and 7); 2) to move closer to the liquid/gas interface in order to compensate the weakening of the magnetic field due to the rotation, in order to apply constant magnetic filed force to the capsule during the rotation (FIG. 8); and 3) to perform rotations between 45-135 degrees when the direction of external magnet field remains relatively small, so that the capsule endoscope will change its tilt angle by following the rotation of the external magnet (FIG. 9); or alternatively, 4) changing the tilt angle of the capsule endoscope by changing the direction of the magnetic filed as long as the mass center and magnetic center of the capsule is less than 2 mm (FIG. 10).

Figures 7, 8:
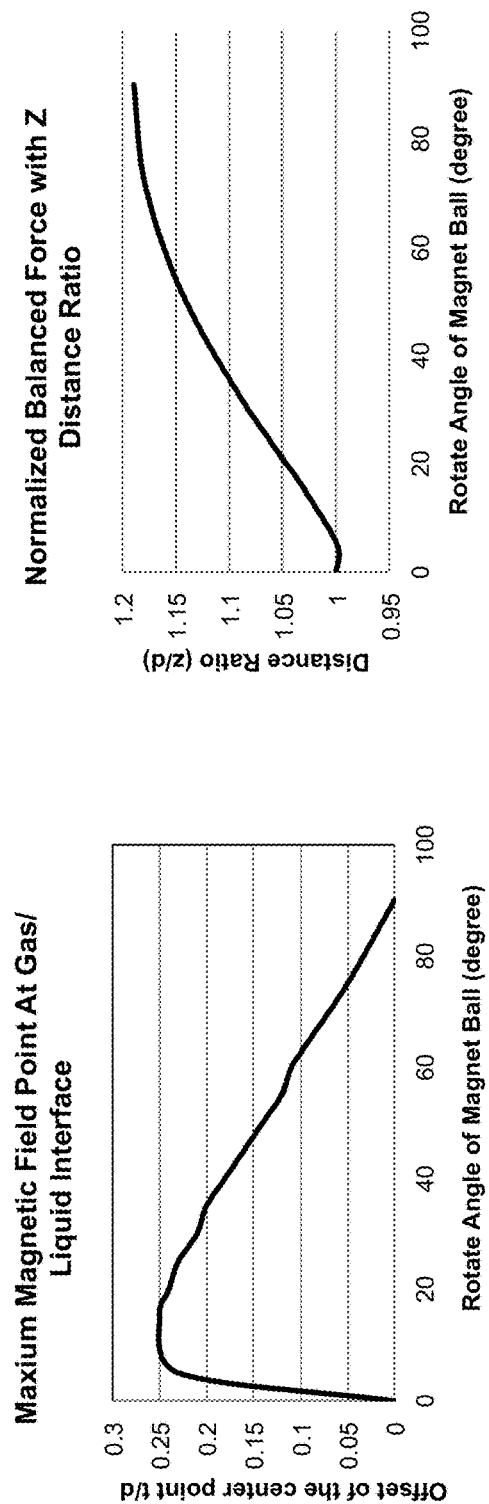
FIG. 7 is an illustration of the relationship between the vertical rotation angle of the magnetic moment of the external magnet and the undesired movement of the capsule endoscope (in a normalized value)
FIG. 8 is an illustration of the relationship between the vertical rotation angle of the magnetic moment of the external magnet and the distance (in a normalized value) along a vertical direction to be adjusted in order to apply constant magnetic field force to the capsule endoscope.

In order to rotate a capsule endoscope to change ONLY its tilt angle, while still maintaining its position, the external robotic magnet in a spherical shape, would have to rotate and translate at the same time. If the external magnet only rotates, the rotational magnetic field generated by the external robotic magnet will not only rotate the capsule endoscope as intended, but also move capsule endoscope in one or both xy coordinates unintentionally, i.e. change the position of the capsule endoscope at the liquid/gas interface, because the maximum magnetic filed on the liquid/gas interface has been altered from one position to another in response to the rotational magnetic field, and the capsule endoscope bearing a permanent magnetic dipole is being attracted to the second maximum magnetic field position in the liquid/gas interface. For example, as shown in FIG. 6, when the external robotic magnetic rotates, the capsule also rotate to change its tilt angle at the liquid/gas interface. At the same time when the rotation occurs, the capsule endoscope moves horizontally from $X_0$ to $X_1$. In FIG. 6, the dashed ellipse is the equal magnetic field line, the tangential point at the gas/liquid interface is the maximum magnetic field point Bm, and the distance from $X_0$ to $X_1$ is the referred as the offset distance t in FIG. 7. FIG. 7 plots a relationship between the rotation angle of the external magnet (degrees) and the undesired movement of the capsule in a normalized x/d format, wherein d is the distance from the center of external magnet to the liquid/gas interface and x is horizontal distance between the magnet center of the capsule endoscope to the projection point of the center of external magnet at the liquid/gas interface, which is the same distance from $X_0$ to $X_1$. According to FIG. 7, when the external magnet in a sphere shape rotates about 10 degrees, the capsule endoscope will move horizontally at a value of x/d at 0.25, which suggests when a distance d is of 30 cm and the capsule endoscope moves to 7.5 cm unintentionally.

However, such unintentional movement in either x or y coordinates is not desired and hence minimized by the method disclosed herein. FIG. 3 shows that capsule endoscope moves in the x or y direction by following the external magnet. In order to the avoid the undesired movement of the capsule endoscope as a result of the rotation of external magnet, the external magnet in the present invention will also move in the x or y direction to offset. The direction of the movement of the external magnet will be in the opposite direction of the undesired capsule movement and the distance of movement of the external magnet will be calculated based on the distance of the undesired movement of the capsule endoscope. In the same selected example in FIG. 7, when the distance d is of 30 cm, and the external magnet rotates 10 degrees, the anticipated 7.5 cm movement to the left of the capsule will be corrected by translating the external magnet further to the right at 7.5 cm, which is equivalent to move the capsule endoscope 7.5 cm to the right. In the control of the suspended capsule, it is directly under the sphere-shaped external magnet when the magnetic moment of the magnet is parallel to the earth, thus it is perpendicular to the liquid/gas interface. When the sphere-shaped external magnet tilts along a horizontal angle, the capsule will exactly follow that the horizontal angle. The plane of line of the capsule's axis and the line of sphere-shaped external magnet magnetization is shown in FIG. 5. The plane is rotating symmetrically. So if we express the compensating translation movement in x,y plane, then $$X = X_0 + t \sin \alpha$$

$$Y = Y_0 + t \cos \alpha$$

wherein $X_0, Y_0$ is the original position of the sphere-shaped external magnet; X,Y is the final position of the sphere-shaped external magnet. α is the horizontal rotation angle, t is the shift distance as shown in FIG. 5.

The translation can happen during the rotation or before/after the rotation. Preferably the external magnet rotates and performs a translation at the same time.

In one embodiment of the present invention, it is disclosed a method to maintain a capsule endoscope at the same position while it rotates, wherein the capsule endoscope is suspended at liquid/gas interface having a first tilt angle. The method includes providing a capsule endoscope comprising a permanent magnetic dipole and a camera;

suspending the capsule endoscope at a liquid/gas interface, wherein the capsule endoscope forms a tilt angle at a liquid/gas interface to observe an internal organ;

applying magnetic field force to the permanent magnet dipole through an external magnet;

changing the angle of the tilt angle while being suspended at the same at the same position at the liquid/gas interface by rotating and moving the external magnet along one or more axially directions.

Further besides maintaining the capsule endoscope at the same position during the translation, it is also desired to subject the capsule endoscope to the same magnetic field force during the rotation process in order to achieve a smooth rotation. When the external magnet rotates, the magnetic field force experienced by the capsule endoscope changes. In order to apply constant magnetic filed force to the capsule endoscope, the distance between the external magnet and magnet capsule need to be changed. The calculation is shown in FIG. 8. FIG. 8 plots a calculation of a distance that the external magnet ball needs to be moved relating to its rotational angle. For example, in a system that the distance d from the center of the sphere shaped external magnet to the gas/liquid interface before the rotation is 30 cm, and when the external magnet intends to rotate 90 degrees, then the external magnet needs to be adjusted along its vertical position to achieve a d/z value at 1.18, which means after the rotation the external magnet is at a position wherein z=d/1.18=30/1.18=25.4 cm. This calculation further suggests that external magnet needs to be brought closer to the liquid/air interface for 30−25.4=4.6 cm.

In another embodiment of the present invention, it is disclosed a method to apply constant magnet field force to a capsule endoscope while it rotates, wherein the capsule endoscope is suspended at liquid/gas interface having a first tilt angle. The method includes providing a capsule endoscope comprising a permanent magnetic dipole and a camera;

suspending the capsule endoscope at a liquid/gas interface, wherein the capsule endoscope forms a tilt angle at a liquid/gas interface to observe an internal organ;

applying magnetic field force to the permanent magnet dipole through an external magnet; and changing the tilt angle of the capsule endoscope while being suspended at the liquid/gas interface by rotating the external magnet; and adjusting the distance between the external magnet and liquid gas interface to apply constant external magnet field force to the capsule endoscope during the rotation.

Figure 9:
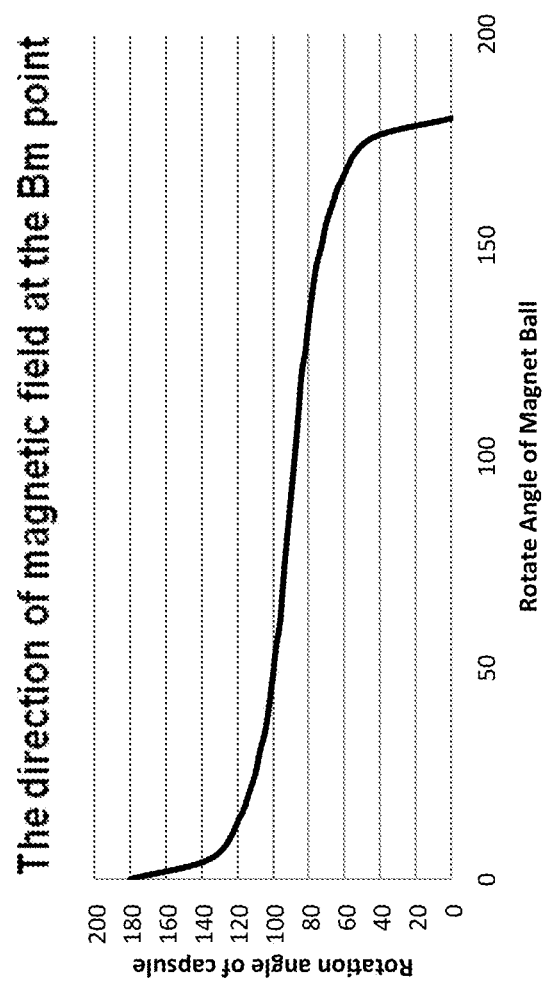
FIG. 9 plots a relationship between rotational angle of the capsule endoscope and the vertical rotation angle of the magnetic moment of the external sphere-shaped magnet.
Figure 10:
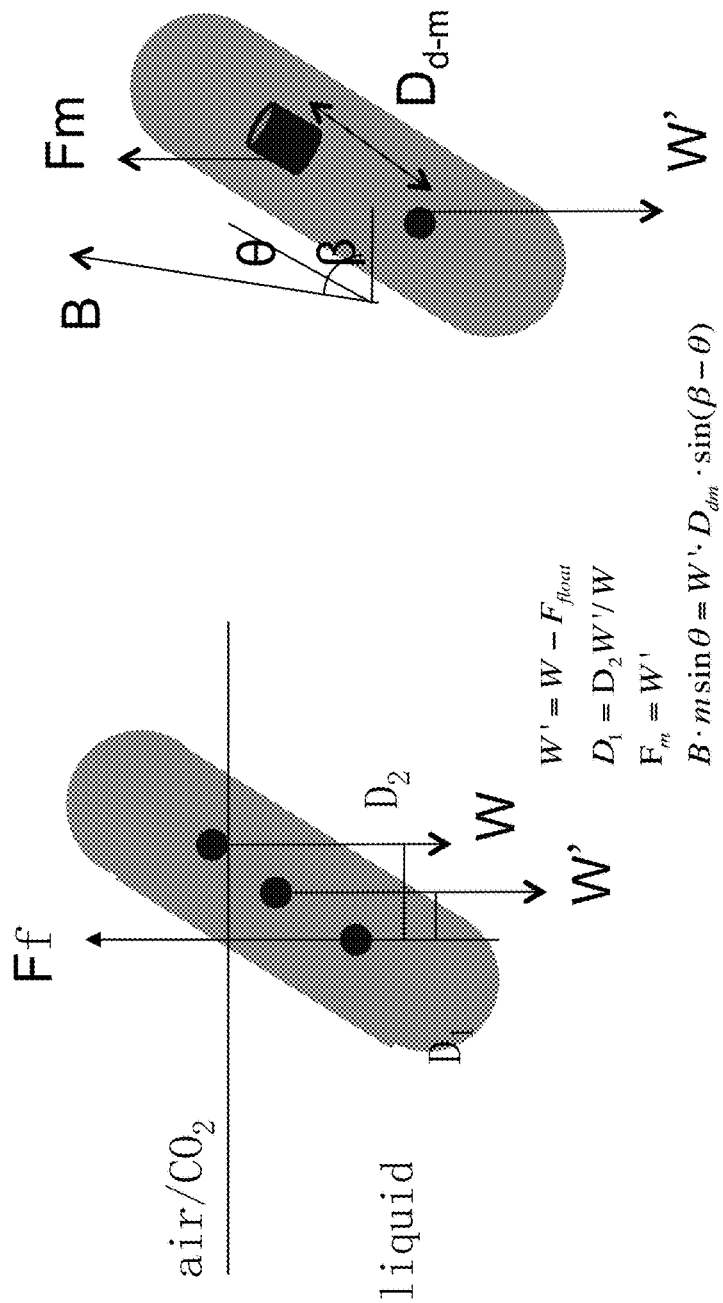
FIG. 10 is a schematic diagram to explain the various force experienced by a capsule endoscope while being suspended at a gas/liquid interface having a tilted angle in accordance with the aspect with the present invention.

Referring to FIG. 9, during the rotation of the external magnet, its magnetic filed direction could also change depending on the rotation angle. In FIG. 9, the y-axis is the field angle (direction) of the external magnetic field at the position of the maximum magnetic field in the gas/liquid interface. When the magnetic field is strong or the capsule weight center and the small magnet dipole center is close, the capsule will follow the external magnetic field direction. By rotating sphere-shaped external magnet, the capsule endoscope tilt angle will change correspondingly. FIG. 9 suggests this angle control is relative easier to if the rotation angle of the capsule between 45 degree and 135 degree.

However sometimes in the clinical settings, maneuver the capsule endoscope through a wide range and accomplish a more horizontal tilt removes the need to reposition the capsule endoscope and allows a quicker and efficient procedure.

In an alternative embodiment of the present invention, if the distance between the magnetic center of capsule and the mass center of the capsule is very small, changing the direction of the external magnetic field can change the tilt angle of the capsule endoscope. In one example, the distance between the magnetic center of capsule and the mass center of the capsule is less than 2 mm. Said magnetic center of the capsule is the center of small magnetic dipole inside the capsule endoscope.

Referring to FIG. 10, the capsule being suspended experiences three forces, $F_{float}$ is the floating force, (W) is the gravity of the capsule and W' is the effective weight of the capsule suspended in the liquid, which is water in this example. $D_1$ is the horizontal distance from the gravity center (mass center) of the liquid occupied or replaced by the part of the capsule to the effective capsule weight center; and $D_2$ is the horizontal distance from the gravity center (mass center) of the liquid occupied by the part of the capsule to the capsule mass center. Further, $F_m$ is magnetic field force on the small magnetic dipole in capsule; B is the magnetic field with the β angle to the horizontal plane, the m is the magnetic moment of the small magnetic dipole inside the capsule. The $D_{dm}$ is the distance between the center of small magnet dipole in the capsule and the effective weight center (mass center) of the capsule. The θ is the additional tilt angle for the line connecting the small magnet and the effective weight center. In a suspension state, the following equations are established (Equations 6-9).

$$W'=W-F_{float} \quad \text{Eq.6}$$

$$D_1=D_2 W'/W \quad \text{Eq.7}$$

$$F_m=W' \quad \text{Eq.8}$$

$$B \cdot m \sin\theta = W' \cdot D_{dm} \cdot \sin(\beta-\theta) \quad \text{Eq.9}$$

It can be derived from the above equations that by changing the direction of external field B, one can control the tilt angle of the floating capsules. Although the effective weight center is changing with immersion volume of capsule, it is still around the mass center. In order to easily control the tilt angle, the $D_{dm}$ should be small, so it is preferred to make the small magnet to be close to the mass center of the capsule, e.g. <2 mm. In one preferred example, when the capsule endoscope has one camera, the distance between the small magnetic dipole and mass center is less than 2 mm. In alternative preferred example, the capsule endoscope has a length of L, and its length is longer than 12 mm when the capsule has two cameras, one on each end of the capsule.

Figure 11:
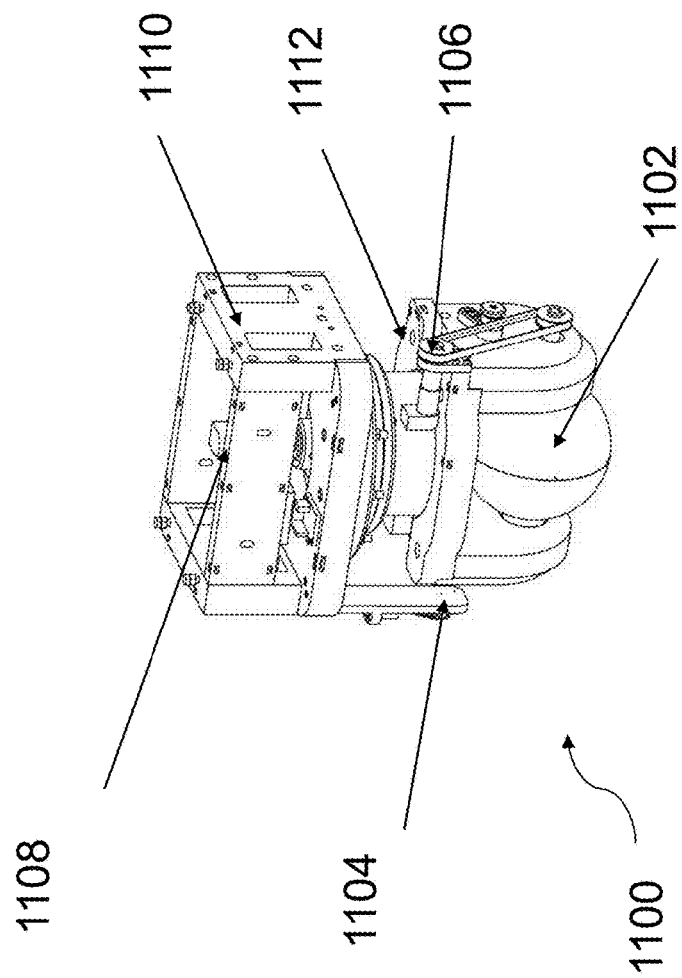
FIG. 11 is an exemplary embodiment of an external robotic magnet, in accordance with the aspect of the present invention.

FIG. 11, shows an exemplary external robotic magnet in accordance with the aspects of the present invention, which provides a sphere-shaped external magnet, allowing translation, vertically movement, horizontal and vertical rotation.

Additional embodiments and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A method to move a capsule endoscope locally, comprising
    providing a capsule endoscope comprising a permanent magnet and a camera;
    suspending the capsule endoscope stably at a liquid/gas interface by an external magnet wherein the capsule endoscope forms a tilt angle at a liquid/gas interface to observe an internal organ;
    applying magnetic field force to the permanent magnet through the external magnet to move the capsule endoscope; and
    rotating the capsule endoscope while being suspended at the same position at the liquid/gas interface by rotating and moving the external magnet along one or more axial directions simultaneously, this step further comprising moving the external magnet to offset the change in position of the capsule endoscope that would occur if the external magnet was rotated without being moved;
    wherein the capsule has a density greater than the density of the liquid.

2. The method of claim 1, further comprising changing the tilt angle of the capsule endoscope by rotating the external magnet between 45-135 degrees.

3. The method of claim 1, further comprising
    the permanent magnet inside the capsule endoscope receives a constant magnitude of magnetic force while the capsule is rotating and being suspended at the liquid/gas interface.

4. The method of claim 3, wherein the step of changing the tilt angle of the capsule endoscope while being suspended at the liquid/gas interface further comprises
    rotating the external magnet and adjusting the distance from the external magnet to the liquid/gas interface simultaneously.

5. The method of claim 1, further comprising
    suspending the capsule endoscope at the liquid gas interface; and
    changing the tilt angle of the capsule endoscope by changing the direction of the external magnetic field.

* * * * *